United States Patent [19]

Young

[11] 4,379,262

[45] Apr. 5, 1983

[54] NUCLEAR MAGNETIC RESONANCE SYSTEMS

[75] Inventor: Ian R. Young, Sunbury-on-Thames, England

[73] Assignee: Picker International Limited, Wembley, England

[21] Appl. No.: 175,672

[22] Filed: Aug. 5, 1980

[30] Foreign Application Priority Data

Aug. 10, 1979 [GB] United Kingdom ................. 7927965

[51] Int. Cl.³ .......................................... G01N 27/00
[52] U.S. Cl. .................................. 324/309; 324/311; 324/313
[58] Field of Search ............... 324/300, 309, 310, 311, 324/313, 320

[56] References Cited

U.S. PATENT DOCUMENTS

| 3,052,834 | 9/1962 | Schuster | 324/313 |
| 4,068,161 | 1/1978 | Ernst | 324/311 |
| 4,115,730 | 9/1978 | Mansfield | 324/309 |
| 4,290,019 | 9/1981 | Hutchison | 324/309 |

FOREIGN PATENT DOCUMENTS 2027208 2/1980 United Kingdom .

*Primary Examiner*—Michael J. Tokar
*Attorney, Agent, or Firm*—Fleit & Jacobson

[57] ABSTRACT

The invention is suitable for a small nuclear magnetic resonance pulse head applicable to a part of the body in the manner of ultrasonic systems. The arrangement generates a field which varies in amplitude with distance from the head, being uniform at surfaces which intrude into the body. Resonance is excited in one such surface and a gradient restricts resonance to one line therein. The phase is then dispersed along the line and the signal sensed as a function of position therealong.

13 Claims, 11 Drawing Figures

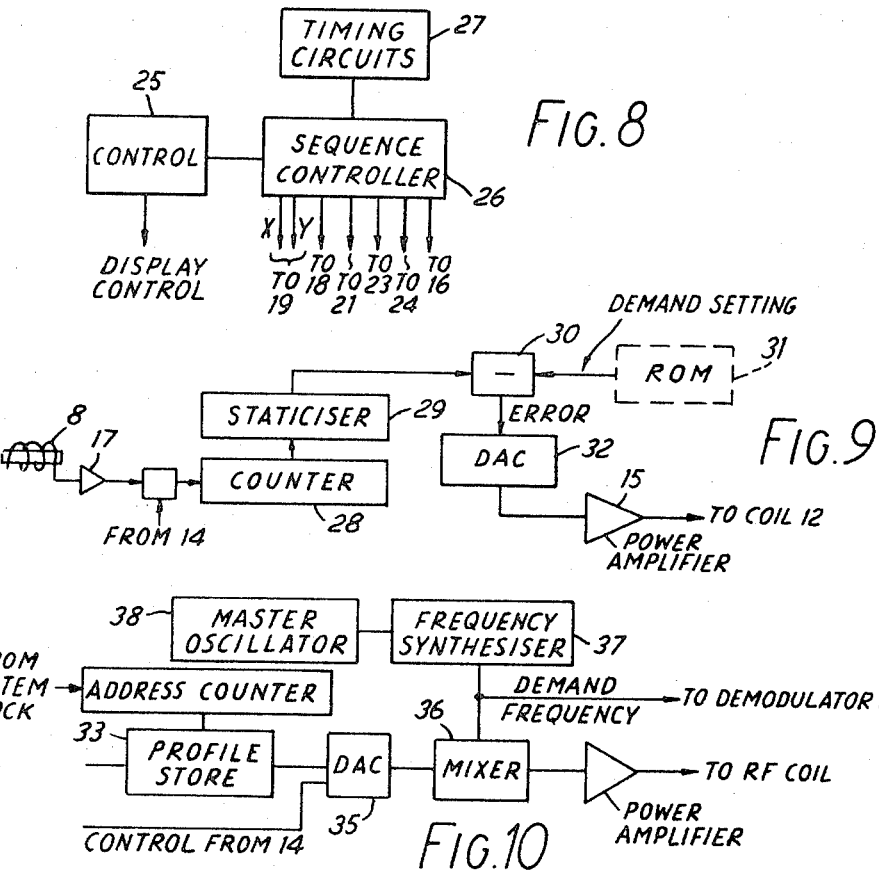
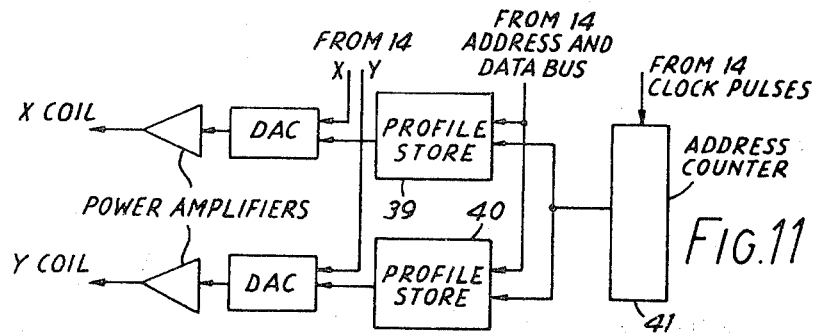

NUCLEAR MAGNETIC RESONANCE SYSTEMS

The present invention relates to systems for examining a body by nuclear magnetic resonance.

Nuclear Magnetic Resonance (NMR) is well known for examination of samples by spectroscopy. Recently it has been proposed to provide images, of sectional slices or selected volumes. These procedures are useful in particular for medical examination of patients.

Such equipment is, however, relatively cumbersome comprising large coil systems which surround the patient.

It is an object of this invention to provide an arrangement incorporating relatively more compact equipment.

According to the invention there is provided a nuclear magnetic resonance apparatus including means for generating a steady magnetic field of strength which varies with distance therefrom, at least in a first direction being uniform at surfaces which can be caused to protrude into a body to be examined, means for exciting resonance for nuclei in the body, coinciding with a chosen surface, means for applying a field having a gradient in a second direction orthogonal to the first direction to restrict resonance to a line in the surface, means for dispersing the phase of the resonance along said line and means for sensing the dispersed resonance as a function of position in said line.

Figure 1:
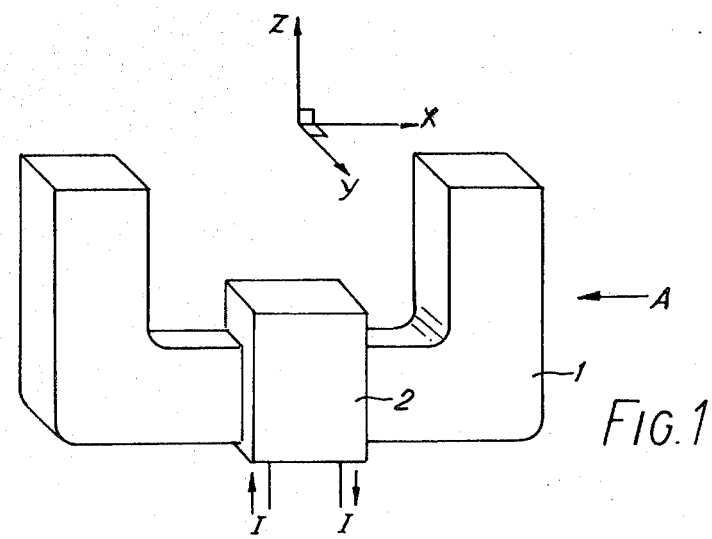
Figure 2:
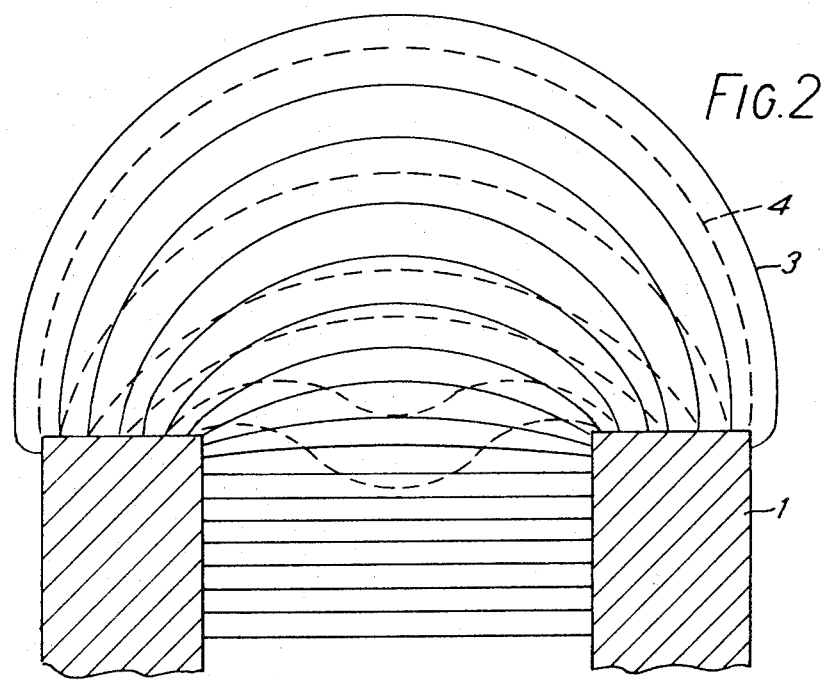
Figure 3:
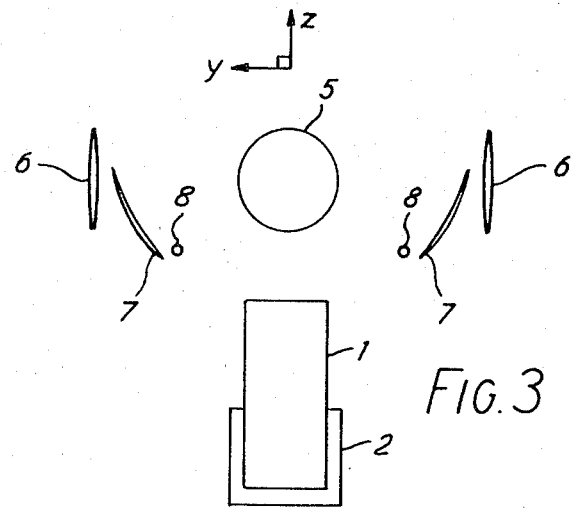
Figure 4:
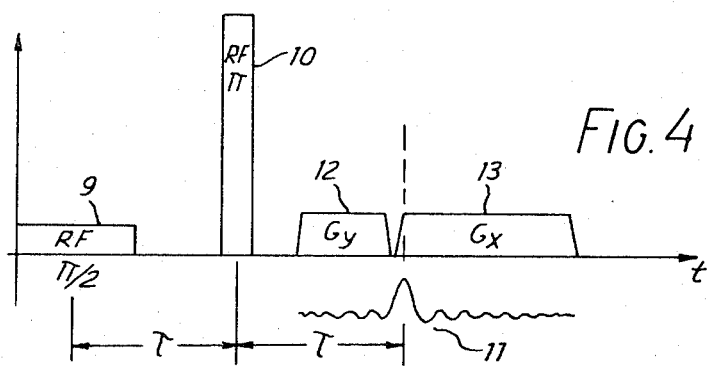
Figures 5, 6:
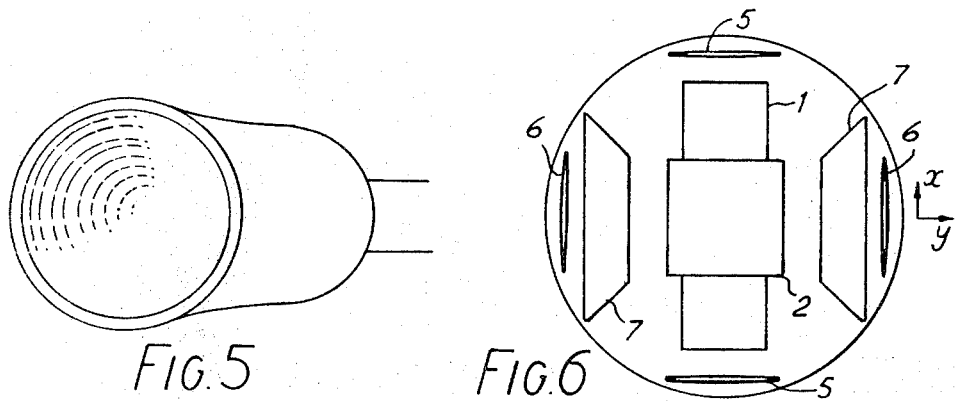
Figure 7:
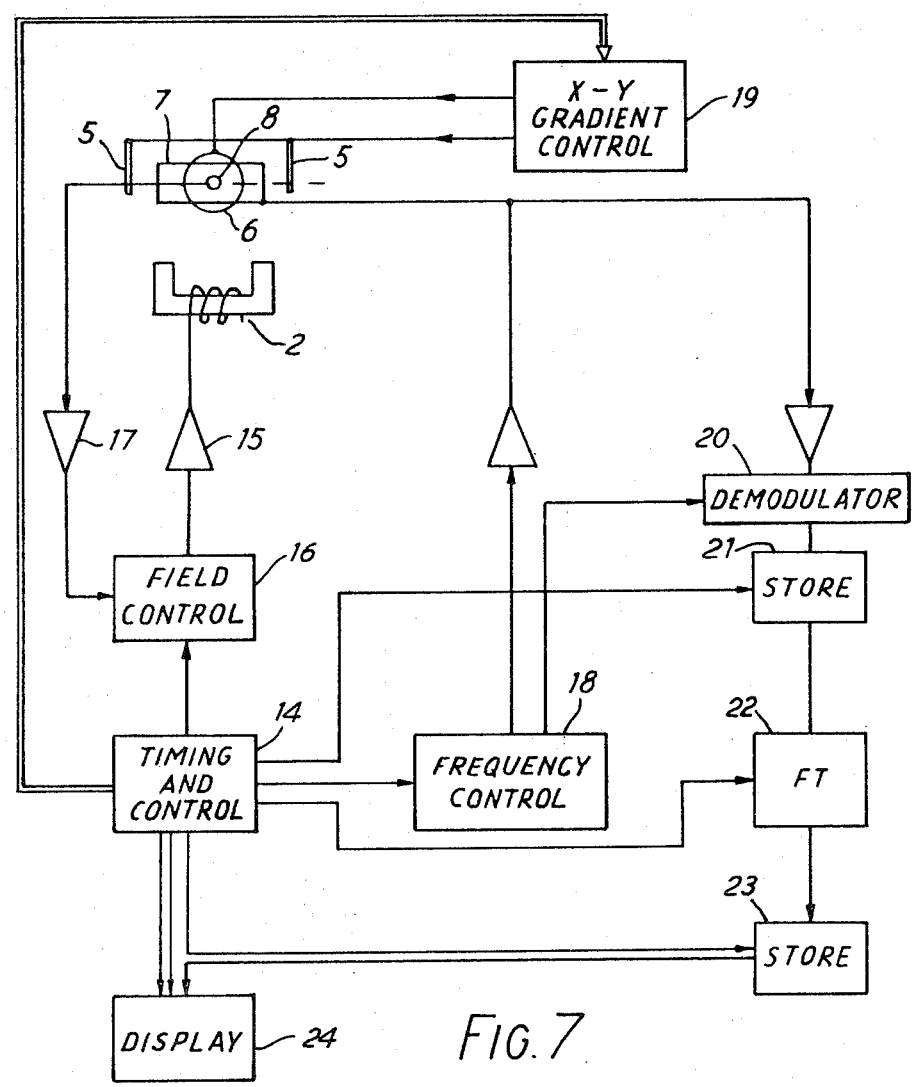

In order that the invention may be clearly understood and readily carried into effect it will now be described by way of example with reference to the accompanying drawings of which, FIG. 1 shows a yoke and coil for providing a Z-field gradient, FIG. 2 shows the nature of the field so produced, FIG. 3 shows the position of the other coils and probes, FIG. 4 shows the examining pulse sequence used, FIG. 5 shows the examining head in perspective view, FIG. 6 shows shows the head in plan view, FIG. 7 is a block diagram of a circuit for the invention, FIG. 8 is a block diagram of the timing and control circuit of FIG. 7, FIG. 9 is a block diagram of the field control cavity of FIG. 7, FIG. 10 is a block diagram of the frequency control circuit and FIG. 11 is a block diagram of the gradient control circuit of FIG. 7.

Nuclei subject to a magnetic field have a resonant frequency related to the value of the field. Then by application of an R.F. Magnetic field at the resonant frequency they can be excited and the excitation allowed to decay. The decay causes an induced signal at the resonant frequency in suitable coils.

Arrangements have been proposed, for example as described in U.S. Pat. Nos. 4,284,950 and 4,254,778, in which the magnetic field is adjusted to have different values in different parts of the body. A basic steady $H_{Zo}$ field in the Z-direction (usually axially of the patient) is applied and also a further $H_Z$ field having a gradient $G_z = \delta H_z/\delta z$. This provides a unique total field value in a chosen cross-sectional slice perpendicular to the Z-axis. Resonance is excited preferentially in this slice and the resonance signal therefrom can be detected. Further field gradients in the plane of the slice are applied to cause dispersion of the resonance frequencies to provide the basis for analysing the signals to relate to different strips in the slice. If this is repeated for different strip patterns in the slice the signals so obtained may be processed to give an image of the slice.

However the coils used surround the patient entirely, being then both massive and expensive.

The invention uses a smaller geometry, at least part of which can be placed in a relatively small probe to be placed near to and to investigate a limited region of the patient in a similar fashion to the procedure known for ultrasonic probes.

The basis of the probe is a magnet shown in FIG. 1 comprising a yoke 1 and a coil 2. This produces a field in the gap area which is non uniform on all three of the axes shown, most significantly in the Z-direction.

FIG. 2 shows the field in the gap, the field lines 3 being shown in solid line and the field contours 4, (lines of constant field) being shown in broken line. FIG. 2 is merely indicative, the positions of the lines not being accurately computed.

The surfaces of constant field, shown in cross-section in FIG. 2, are in fact curved surfaces, symmetrical in principle about the x and y axes. They are very complex at the poles but it is not intended to make use of fields close to the poles.

FIG. 3 shows a view of the probe from the direction A in FIG. 1. Also shown are: coils 5 which provide a field having a gradient Gx in the x-direction; 6, which produce a gradient Gy in the y-direction; 7, which produce an R.F. field; and field sensing probes 8, which are of conventional type such as NMR probes.

Initially current is applied to coil 2 and is held so that the field is as nearly constant with time as is practicable, using the field probes 8 for a reference. This produces a gradient in field as shown in FIG. 2. Following conventional NMR principles each surface of constant field has a respective resonance frequency for a particular substance. One of these is selected and there is applied an R.F. pulse at the resonant frequency for that surface. This is shown at 9 in FIG. 4 which shows the complete pulse sequence.

It will be understood that the effect of the steady magnetic field is to cause nuclei, of the substances being investigated, to align their spins in the field direction. The R.F. field causes the spins to precess about the field direction with a precession angle which increases with increasing RF field envelope integral. It is usual to identify the R.F. pulse with the precession angle it produces so that a $\pi/2$ pulse produces a 90° angle and a $\pi$ pulse produces a 180° angle.

In this example pulse 9 is a $\pi/2$ pulse. It should be noted that the longer the pulse, the thinner is the surface which is excited as more dephasing occurs due to the Z-gradient. Of course the height must be decreased to maintain the same precession angle.

After a time $\tau$ a short 180° RF pulse 10 is applied to rephase the spins and produce a 'spin-echo' as is now well known in NMR. The spin echo itself will, following known principles, occur after a further delay of $\tau$ equal to that between the $\pi/2$ and $\pi$ pulses. The Z-gradient may be maintained during pulse 10 although that is not essential. Thereafter the current in coil 2 is stopped so that the Z-gradient is removed, leaving the nuclei in the chosen shell resonating. After the $\pi$ pulse 10 but before the spin echo occurs there is applied an y-gradient pulse 12 on coils 6. This disperses the phases of the nuclei except along the Gy=0 line at which the resonance is maintained at the same frequency and phase. Thus, the spin echo, when it occurs, will be detected only on the line at which Gy=0.

After time $\tau$ from the $\pi$ pulse 10, the spin echo is detected by signal induced in this example in the RF coils 7, which are tuned to the appropriate frequency, although other specially designed coils could be used. As the spin echo occurs, however, there is applied an x-gradient pulse 13 which disperses the spins along the selected line during the FID. The FID is then Fourier Transformed to give a signal which varies with position along the line.

It will be appreciated that the line evaluated will be curved and not straight and the position may not be known with the accuracy of the larger machines. It will, however, give a useful indication of the quantity being measured which, by application of the probe external to a region of interest, can give at least a spot diagnosis of a gross condition.

The lines can be evaluated at different orientations and can be processed to give an image in the manner of prior art apparatuses.

The quantity being evaluated may be proton density, for water content, or may be density of nuclei of, say, Potassium, Phosphorus, Ferros Sulphate, Sodium, Barium etc. It may be relaxation time.

FIG. 5 shows a perspective view of the examining head enclosed in an outer case. FIG. 6 is a plan view of the head showing the internal disposition of the coils and corresponding to the side elevation of FIG. 3. A typical head giving a field of about 0.1 Tesla over a volume of 200 mm$^3$ may weigh 400 kg and will typically be 1000 mm diameter by 700 mm long, so that it should be counterpoised on a moving gantry, not shown, in the manner of large conventional x-ray equipment.

FIG. 7 shows a block diagram of the complete system. A timing and control unit 14 includes in read only memory the start and stop times, together with precalculated amplitudes and frequencies for the pulses. It controls coils 2 via an amplifier 15 to give the steady field and Z-gradient. A field control 16 receives, via amplifier 17 signals from probes 8 and merely compares these with the instructed field and alters the coil current appropriately.

The frequency on the RF coils 7 is set by a frequency control 18. This includes an R.F. oscillator whose timing and frequency are set from control 14. It should be noted that control 14 may include an operator input so that the field may be swept for a search procedure.

Similarly the x and y gradients are set by field drive and control unit 19, in response to control 14.

The signals sensed in the R.F. coils are demodulated in a known type of demodulator 20. They are then taken into a RAM store 21 at the appropriate time. From there they are Fourier transformed in circuits 22, and entered into a further store 23. Stores 21 and 23 may be the same unit.

The output may be displayed on a suitable display 24.

The individual circuit elements shown in FIG. 7 are conventional to those familiar with nuclear magnetic resonance imaging and circuits for the control of similar equipment. However for further clarification suitable circuits for implementation of elements 14, 16, 18 and 19 are shown in block diagrammatic form in FIGS. 8, 9, 10 and 11 respectively.

FIG. 8 then shows in more detail the timing and control arrangement 14. The control block shown at 25 provides the basic control input for the apparatus. This may simply be an operator control panel at which the operator selects the next operation required or may be a microprocessor holding a predetermined control pattern but will generally be a combination of those two. The control 25 supplies instructions to a sequence controller 26. This holds in read only memory a predetermined bit pattern array representing instruction pulses for each of the output lines for each instruction and provides these pulses at timing pulses from timing circuits 27 in response to instructions from 25. Circuits 27 comprise a system clock and appropriate counters and gates. It will be understood that circuits of this form are well known for controlling any sequence of operations which is known in advance and can readily be adapted to a chosen examination procedure.

The field control 16 shown in FIG. 9 gates the field probe output from amplifier 17 with timing signals from 14 and takes a count in counter 28 which is in fact the measured field. Held in a staticiser 29, the measured field is compared in a subtractor 30 with the precalculated field (demand setting) from a store such as a read only memory 31. The consequent error signal is digitised in unit 32 to be applied to coil 12 via power amplifier is thereby to bring the field to the required value.

FIG. 10 illustrates the frequency coil of unit 18. The RF field pulses 9 and 10 of FIG. 4 are held in a profile store 33 as a sequence of amplitudes of the RF envelope at different times, these being precalculated for an examining sequence. The system clock in unit 14 provides pulses to a programmed address counter 34 which causes unit 33 to output the required amplitude sequence. A digital to analogue converter 35 controlled from 14 applies to these to a mixer 36 where they are mixed with the RF from frequency synthesizer 37 fed by a master oscillator 38. The mixed signal is fed to the RF coil while the RF from 37 is supplied to the demodulator 20.

Gradient control 19, as shown in FIG. 11 also uses profile stores 39 and 40 holding the Gx and Gy pulse profiles also as precalculated amplitudes at different times. The profiles are clocked out with instructions timed by sequences 26 in unit 14, and clock pulses via address counter 41. These simply provide the digital amplitudes which are then converted to analogue form and amplified for application to the x and y coils.

In the foregoing circuits all of the stores holding timing sequences and profiles may be read only memory. However it will be appreciated that use of reprogrammable memories will allow the pulse sequence to be altered to modify the examination procedure to need.

Other embodiments of the invention will be apparent to those experienced with nuclear magnetic resonance.

What I claim is:

1. A nuclear magnetic resonance apparatus comprising:
    first magnetic means for generating a steady magnetic field which bulges outwardly from one side of said first magnetic means so as to protrude into a body positioned adjacent said first magnetic means on said one side, thereby to establish therein a magnetic field which varies in strength with distance in at least a first direction in said body and is of constant strength in curved surfaces in said body;
    means for preferentially exciting resonance of nuclei within the body lying in a selected one of said curved surfaces of constant magnetic field strength;

second magnetic means for applying a magnetic field having a gradient in a second direction orthogonal to said first direction, thereby to restrict resonance to a line in said one surface wherein said one surface intersects a surface in which the magnetic field produced by said second magnetic means is constant;

means for dispersing the phase of the resonance along said line; and means for sensing the dispersed resonance as a function of position in said line.

2. A method of examining a body by nuclear magnetic resonance, the method including:

applying to the body from one side only thereof a steady magnetic field which protrudes into the body from said one side so as to provide within the body a magnetic field which varies in strength with distance in at least a first direction in said body and which is of constant strength in curved surfaces in said body;

preferentially exciting resonance of nuclei within the body lying on selected one of said surfaces;

applying a second magnetic field to said body having a gradient in a second direction orthogonal to said first direction, thereby to restrict resonance to a line on said one surface wherein said one surface intersects a surface on which the second applied magnetic field is constant;

dispersing the phase of the resonance along said line; and sensing the dispersed resonance as a function of position in said line.

3. An apparatus according to claim 1 wherein said first magnetic means comprises a U-shaped yoke and a coil arranged to energise the U-shaped yoke to provide, in an area adjacent the gap between the ends of the yoke, said steady magnetic field.

4. An apparatus according to claim 1 or claim 3 wherein said means for exciting resonance includes a coil system cooperating with drive circuits arranged to generate an RF field.

5. An apparatus according to claim 4 wherein said RF coil system also forms part of said means for sensing the dispersed resonance.

6. An apparatus according to claim 1 wherein said means for dispersing include means for generating a further magnetic field having a gradient substantially orthogonal to said first and second directions.

7. An apparatus according to claim 6 wherein said means for generating said further field include field coils.

8. An apparatus according to claim 1 including Fourier Transform means arranged to cooperate with the means for sensing the dispersed resonance to provide signals representing amplitudes of resonance for different positions in said line.

9. An apparatus according to claim 1 including a mobile probe which includes coils for generating said fields and sensing said resonance signals.

10. A method according to claim 2 wherein said resonance is excited by application of an RF magnetic field having a first pulse envelope.

11. A method according to claim 10 wherein said first pulse envelope is followed by a second pulse envelope of said RF field to cause a spin echo of said resonance.

12. A method according to claim 11 wherein the first pulse envelope provides a $\pi/2$ pulse and the second pulse envelope provides a $\pi$ pulse.

13. A method according to claim 11 or claim 12 wherein said second magnetic field is applied prior to said spin echo and the said dispersion is obtained by applying to said body, immediately following said spin echo, a third magnetic field having a gradient in a direction orthogonal to said first and second directions.

* * * * *